United States Patent [19]

Worschischek et al.

[11] 4,251,212
[45] Feb. 17, 1981

[54] DENTAL HANDPIECE

[75] Inventors: Rainer Worschischek, Lorsch; Werner Schuss, Heppenheim, both of Fed. Rep. of Germany

[73] Assignee: Siemens Aktiengesellschaft, Berlin & Munich, Fed. Rep. of Germany

[21] Appl. No.: 102,446

[22] Filed: Dec. 11, 1979

[30] Foreign Application Priority Data

Dec. 22, 1978 [DE] Fed. Rep. of Germany ....... 2855874

[51] Int. Cl.³ .............................................. A61C 1/08
[52] U.S. Cl. .................................... 433/126; 433/116
[58] Field of Search ............... 433/126, 131, 130, 133, 433/146

[56] References Cited

U.S. PATENT DOCUMENTS

| | | | |
|---|---|---|---|
| 866,518 | 9/1907 | Repsold | 433/116 |
| 2,041,077 | 5/1936 | Lininger | 433/116 |
| 2,370,632 | 3/1945 | Blair | 433/133 |
| 3,436,980 | 4/1969 | Loge et al. | 74/352 |
| 3,487,546 | 1/1970 | Beierlein et al. | 433/104 |
| 3,657,818 | 4/1972 | Garnier | 433/131 |
| 3,909,946 | 10/1975 | Watonabe | 433/126 |
| 4,007,529 | 2/1977 | Fleer | 433/104 |

FOREIGN PATENT DOCUMENTS 2653588 6/1978 Fed. Rep. of Germany ........... 433/104

*Primary Examiner*—Robert Peshock
*Assistant Examiner*—John J. Wilson
*Attorney, Agent, or Firm*—Hill, Van Santen, Steadman, Chiara & Simpson

[57] ABSTRACT

A dental handpiece having a first section rotatably mounted on an axis of a drive motor part and supporting a head part at the other end, characterized by the head part being releasably connected to the first section and a rotatable coupling in the cooling lines between the drive motor part and the first section being free from uncoupling when changing the head part to change the drive ratio of the drive train. In addition, the head part has a protective sleeve which surrounds the first section and the rotatable coupling so that the rotatable coupling and first section are not subjected to sterilization with adverse effects to the coupling and to the condition of the lubricant in the various bearings in the drive train.

4 Claims, 3 Drawing Figures

DENTAL HANDPIECE

BACKGROUND OF THE INVENTION

The present invention is directed to a dental handpiece which has a drive motor part and a handpiece part which is mounted for rotation on a longitudinal axis of the motor part. The handpiece part contains a first section, which is releasably secured for rotation on the drive motor part and supports a drive train for transferring rotary motion of the drive motor to a socket in a head part, which socket mounts a tool for rotary motion on the axis of the tool. Cooling lines extend through the motor part and a rotary coupling into the first section and then to the head part for discharge adjacent to the so claimed tool. The rotatable coupling is in the rotational joint between a portion of the first section and the motor part and includes an annular groove in one of the two rotatable members and a passage in the other member in communication with the groove.

Dental handpieces, which have a drive motor part, a handpiece part, which is composed of a first section mounted for rotation on the longitudinal axis of the motor part and has a head portion at the other end with a drive train which is formed of drive shaft sections for conveying the rotary motion of the drive motor to a socket which mounts a tool for rotation on an axis, are known. A rotational connection between the first section and the motor part is usually formed by means of a snap ring groove which on one hand insures rotatably but prevents axial shifting of the first section on the drive motor part. The cooling agent transmission lines from the drive motor to the handpiece part employs a rotatable coupling at the rotational connection or rotary joint therebetween. The rotatable coupling essentially consists of an annular groove for each cooling agent line which groove is sealed on both sides by means of O rings and is in communication with a passageway of the other part. For example, the annular groove may be provided in a guide shank which surrounds the drive shaft of the drive motor and an axial or radial channels are in communication with the annular groove and are formed in the other part which is telescopically received onto the guide shank. A reverse arrangement of the rotatable coupling parts is also possible so that the annular groove are on the handpiece part which is telescoped onto the guide shank which is provided with radial channels.

In these dental handpieces, the rotatable coupling is also released when the two handpiece parts, for example the first section is removed or disconnected from the drive motor part. The coupling and uncoupling of the handpiece parts, which is carried out frequently in order to change the various head pieces used with a drive motor, cause a great wear of the rotatable coupling parts, particularly at the O ring seals. Moreover, while in an uncoupled state, there is a danger that dirt can penetrate into the openings of the radial passages and into the annular grooves of the rotatable coupling to the detriment of the flow of the cooling agent which may be interrupted by these particles.

Another problem is present by the requirements for sterilization particularly sterilization of the head part and the grip section which sterilization is accomplished in an autoclave. Thus, the sealing rings are subjected to high temperatures which are detrimental to their sealing capabilities and in addition, glued joints which are often present at the bearings may be damaged and the bearing lubricants may be washed away. Due to the washing out of the lubricants for the bearings during the sterilization operation, the bearings must be lubricated after every sterilization process.

SUMMARY OF THE INVENTION

The present invention is directed to providing a specific dental handpiece, which is improved in comparison to the known handpieces particularly in view of reducing mechanical and thermal loading of the parts which are subject to wear and to reduce the adverse affects of sterilizing the handpiece on the drive shaft and bearing parts in the interior of the dental handpiece particularly the removal of lubricant from the bearings.

To accomplish these tasks, the present invention is directed to an improvement in a dental handpiece having a handpiece part, a drive motor part and means for mounting the handpiece part on the drive motor part for rotation on a longitudinal axis thereof, said handpiece part containing a first section adjacent the drive motor part containing means for supporting the drive shaft section connected with the drive shaft of the motored part, said first section at the other end having a head part having a socket for mounting a tool for rotation, said head part having a drive shaft section coupled to the drive shaft section of the first section to form drive train means for transferring rotary motion of the drive motor to the socket, said drive motor part, first section and head part having means forming a cooling agent line for conveying at least one cooling agent from a supply line through the drive motor part, the first section to a nozzle in said head part for discharge adjacent the tool, said cooling agent means including a rotatable coupling at said means for mounting between the cooling agent line section in the drive motor and the first section, said rotatable coupling being formed by a pair of relative rotatable members with one member having an annular groove in communication with a passage in the other member. The improvement comprises said pair of members being a tubular member in the first section and a bushing member secured to the drive motor part, said tubular member being coaxial with the drive shaft section and being releasably connected to the bushing member for rotation on said longitudinal axis, said head part having a protective sleeve surrounding the tubular member and said rotatable coupling, said handpiece including a releasable lock-in means for releasably holding the protective sleeve and head part on the tubular member of the first section, said lock-in means securing the sleeve member and head part against twisting and axial slippage relative to the tubular member, and plug type means for connecting the cooling section contained in the tubular member to the cooling lines in the head part so that removal of the head part does not uncouple the rotatable coupling.

Thus, the improvement comprises the rotatable coupling being formed by parts which are releasably connected together but which are normally maintained with the drive motor part and are not normally disconnected when the head part is removed. In order to form a connection between the cooling lines of the head part and of the first section, plug-in type connecting means are utilized and the entire tubular member of the first section and the rotary coupling are protected from the exterior by a protective sleeve which is associated with the head part.

Significant advantages of the invention are that the rotatable coupling is no longer subjected to shear stresses in an axial direction by being coupled and uncoupled during each interchanging of the head parts. The transfer location of the rotatable coupling will remain closed when the handpiece part such as the head part is interchanged and thus protected against the penetration of dust and dirt. This protection, which is due to remaining coupled, is due to the fact that the rotatable coupling remains undisturbed when removing the head part to change the prticular drive train relationship such as to change from a step down ratio to a step up ratio.

Another advantage of the present invention is that during sterilization, the parts of the handpiece, such as the means for supporting the drive shaft sections of the first section and the motor section are not subjected to sterilization since the protective sleeve is removed therefrom for purposes of sterilization. Thus, the requirements of repeated lubrication after each sterilization operation are removed.

DESCRIPTION OF THE PREFERRED EMBODIMENTS

Figure 1:
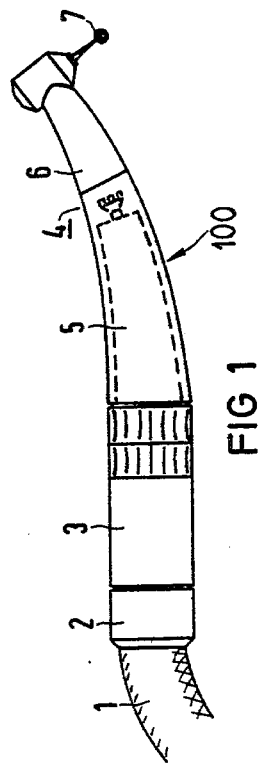
FIG. 1 is a side view of a dental handpiece in accordance with the present invention.

The principles of the present invention are particularly useful in a dental handpiece generally indicated at 100 in FIG. 1. The handpiece 100 has a drive motor part or section 3, which contains an electric micro-motor and is connected to a supply hose 1 by a connector 2. The supply hose 1 provides electricity for the motor and also provides cooling fluids. The drive motor part 3 is connected to a handpiece part 4, which is composed of a first section or part 5 adjacent to the drive motor 3 and a head part 6 which has a socket for mounting a tool 7 for rotation. As illustrated, the handpiece part 4 is mounted on the drive motor part 3 for rotation on a longitudinal axis of the drive motor which axis is defined by the drive shaft 9 (FIG. 2).

Figure 2:
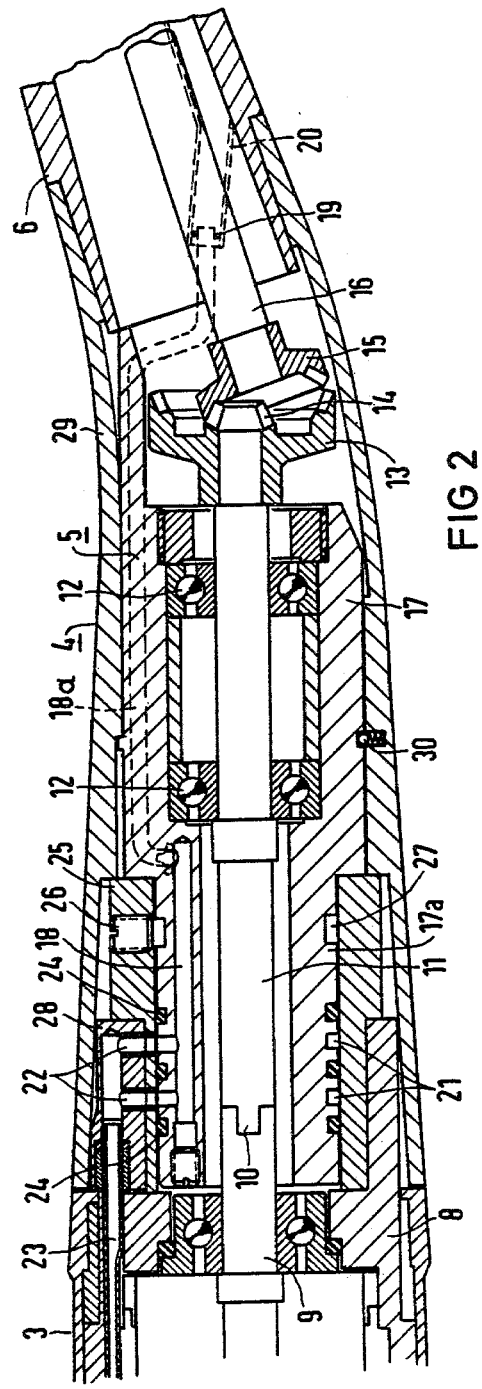
FIG. 2 is a longitudinal cross section of a portion of a handpiece of FIG. 1.

As best illustrated in FIG. 2, the drive motor part 3 has the drive shaft 9, which is mounted for rotation in the housing 8. The drive shaft 9 is connected by a dog clutch 10 with a drive shaft section 11, which is supported by bearings 12 and terminates in the pair of drive gears 13 and 14 at its free end. The drive pinon or gear 14 is engaged with the gear 15 on a drive shaft section 16 of the head part 6. The drive shaft sections 11 and 16 along with the gears which are coupled them together form a gear train for transferring the rotary motion of the motor to the socket containing the tool 7.

Figure 3:
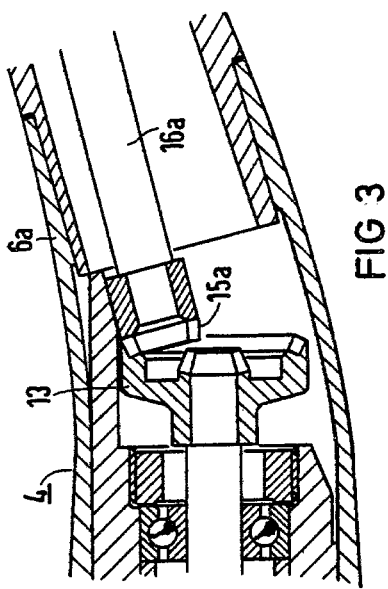
FIG. 3 is a portion of a longitudinal cross section similar to FIG. 2 of an embodiment of the handpiece having a different head part.

When a different head part 6a (FIG. 3) is secured on the first section 5, the other drive gear 13 is engaged by a gear 15a of the drive shaft 16a. Thus, a step up ratio is obtained by the gear arrangement 13 and 15a whereas the gears 14 and 15 provide a step down ratio.

The first part or section 5 is formed by a tubular member 17, which supports the bearing 12 to form the means for supporting the drive shaft section 11. The tubular member 17 also has axially extending passages such as 18 and 18a with the passage 18a being connected by a plug-in connection 19, which includes an O-ring, to a cooling line 20 in the head part 6. The portion 18 is in communication with annular grooves 21, which are formed on an end section or portion 17a. The grooves 21 are in communication with radially extending passages or passageways 22, which are provided in a bushing member 25, that is secured to the housing 8 of the drive motor part. The bushing member 25 along with the tubular member 17 form a rotatable coupling for the cooling line so that the cooling line 23 in the motor part can be coupled to the cooling line 18 to deliver a cooling medium to the cooling line 20 in the head part 6. To prevent leakage around the annular grooves 21, 0-rings such as 24 are provided.

Depending on how many cooling agents are to be supplied to the head part and whether these are to be supplied separately or in a common cooling line, the rotatable coupling is approximately designed to provide the necessary coupling for each separate cooling line. If for example, two agents are to be supplied separately to the head part, then two separate cooling lines 18 are to be provided in the tubular member 17 and are connected by separate radial passageways 22 to separate cooling lines 23 in the motor part 3. As illustrated, the coupling includes the end section 17a telescopically received in a socket formed by the bushing member 25. To detachably connect the two members together, a guide pin 26, which is threaded in bushing 25, is received in a groove 27 formed in the tubular member 17 and this allows rotational movement betwen the two members but prevents axial displacement.

As illustrated, two radial channels 22 and a cross channel to the cooling lines section 23 connecting the two channels are contained in an insert 28 which is received in the bushing member 25.

The parts, such as the tubular member 17 with the drive shaft section 11, the gears 13 and 14 and the bushing 25 form a unit which is associated with the drive motor part 3 and can be easily released for the purpose of service work but remains with the drive motor when the head part 6 is removed to change the drive train ratio. As illustrated, the head part 6 has secured thereto a protective sleeve 29, which telescopically covers and receives the member 17, and the rotatable coupling formed by the tubular member 17 and the bushing 25 and their associated parts. The sleeve 29 is detachably connected on the first section 5, which it completely covers, by means of a lock-in mechanism 30, which mechanism prevents twisting but enables releasing of the sleeve 29 and the head part 6. As illustrated, the lock-in mechanism 30 is formed by a ball detent received in a depression and may include an additional pin guided in a longitudinal extending groove, which pin and groove are provided in a known manner. If desired, the lock-in mechanism may take the form disclosed in copending U.S. Pat. application, Ser. No. 104,980, filed Dec. 18, 1979 which was based on the German Patent P 28 55 682.3. For releasing the handpiece part 6 with the sleeve 29 attached thereto the lock-in mechanism 30 need only be unlocked by means of axially pulling the part 6 and sleeve 29 off of the first part 5. After the head part 6 is removed, portions of the first section 5, for example the bushing member 25 together with the insert 28 and the tubular member 17 with the drive shaft section 11 and the bearings 12 will remain with the drive motor part 3. These parts thus are not effected by the coupling and uncoupling operation of the head part 6 or 6a from the first section 5.

In the present sample embodiment, the drive shaft 9 is connected with the drive shaft 11 by a dog clutch 10. Instead of a two piece division, a continuous, single piece drive shaft can also be advantageously provided and a bushing member which is rigidly connected to the housing 8 of the drive motor part 3 may telescopically extend along the extended drive shaft. In such an instance, the first section will include a tubular member telescopically received on this bushing member to form the rotatable coupling which coupling will have the annular groove and passages for each of the cooling lines. Again, the two parts forming the rotatable coupling can be removed for serviceing but as in the illustrated embodiment, special tools for releasing the stop such as the threaded pin 26 will be required.

Although various minor modifications may be suggested by those versed in the art, it should be understood that we wish to embody within the scope of the patent granted hereon, all such modifications as reasonably and properly come within the scope or our contribution to the art.

We claim:

1. In a dental handpiece having a handpiece part, a drive motor part and means for mounting the handpiece part on the drive motor part for rotation on a longitudinal axis thereof, said handpiece part containing a first section adjacent the drive motor part containing a means for supporting a drive shaft section connected with the drive shaft of the drive motor part, said first section at the other end having a head part having a socket for mounting a tool for rotation, said head part having a drive shaft section coupled to the drive shaft section of the first section to form drive train means for transferring rotary motion of the drive motor to the socket, said drive motor part, first section and head part having means for forming a cooling agent line for conveying at least one cooling agent from a supply line through the drive motor part, the first section to a nozzle in said head part for discharge adjacent the tool, said cooling agent means including a rotatable coupling at said means for mounting between the cooling agent line sections in the drive motor part and the first section, said rotatable coupling being formed by a pair of relative rotatable members with one member being an angular groove in communication with a passage in the other member the improvements comprising said pair of members being a tubular member in the first section and a bushing member secured to the motor part, said tubular member being coaxial with the drive shaft section and being releasably connected to the bushing member for rotation on said longitudinal axis, said head part having a protective sleeve surrounding the tubular member and said rotatable coupling, said handpiece including a releasable lock-in means for releasably holding the protective sleeve and head part on the tubular member of the first section, said lock-in means securing the sleeve member and head part against twisting and axial slippage relative to the tubular member and plug type means for connecting the cooling lines section contained in the tubular member to the cooling lines in the head part so that removal of the head part does not uncouple the rotatable coupling.

2. In a dental handpiece according to claim 1, wherein the rotatable coupling is formed by the bushing member receiving an end of the tubular member of the first section, one of the tubular members and the bushing members being provided with the annular groove and the other of the pair of members being provided with a radial passageway to form the rotatable coupling of the cooling lines.

3. In a dental handpiece according to claim 2, wherein the end of the tubular member is telescopically received in a socket of the bushing member, said tubular member having bearings from the means for supporting the drive shaft section and having passageways terminating in the annular groove which is in communication with a radial passageway in said bushing member.

4. In a dental handpiece according to claim 1, wherein said drive shaft of the drive motor extends into the tubular member of the first section and forms a drive shaft section therein, said bushing member and an end of the tubular member being telescoped together to form the rotatable coupling, said bushing member and tubular member being releasably connected together for axial rotation by a stop dispersed in an annular groove and said protective sleeve extending over the stop and annular groove and exposing said stop and groove when removed with said head part.

* * * * *